United States Patent [19]

Van Dijk et al.

[11] Patent Number: 5,283,069
[45] Date of Patent: Feb. 1, 1994

[54] PRODUCTION OF AROMA AND/OR FLAVOR MATERIALS WITH LACTIC ACID BACTERIA SUPPORTED ON AN EXPANDED, CEREAL ADSORBENT

[75] Inventors: Wietse Van Dijk, Klaaswaal; Bartholomeus J. Van Schie, Leiden, both of Netherlands; Nigel K. H. Slater, Seven Oaks, Great Britain

[73] Assignee: Unilever Patent Holdings B.V., Rotterdam, Netherlands

[21] Appl. No.: 932,295

[22] Filed: Aug. 19, 1992

Related U.S. Application Data

[62] Division of Ser. No. 601,129, Oct. 23, 1990, abandoned.

[30] Foreign Application Priority Data

Oct. 23, 1989 [GB] United Kingdom ............ 8923841.4

[51] Int. Cl.$^5$ .................. A21D 8/02; A23L 1/221; C12N 11/10; C12N 1/20
[52] U.S. Cl. ........................................ 426/18; 426/61; 426/549; 426/650; 435/178; 435/252.9; 435/260; 435/855
[58] Field of Search ................ 435/174, 178, 252.9, 435/260, 855; 426/18, 61, 549, 650

[56] References Cited

U.S. PATENT DOCUMENTS

| | | | |
|---|---|---|---|
| 3,677,897 | 7/1972 | Jeffreys | 195/55 |
| 3,891,773 | 6/1975 | Kline et al. | 435/252.9 |
| 4,056,637 | 11/1977 | Hagiwara et al. | 426/52 |
| 4,927,763 | 5/1990 | Sudoma et al. | 435/260 |

FOREIGN PATENT DOCUMENTS

| | | |
|---|---|---|
| 0298605 | 1/1989 | European Pat. Off. |
| 0303460 | 2/1989 | European Pat. Off. |
| 357427 | of 1987 | U.S.S.R. |

*Primary Examiner*—David M. Naff
*Attorney, Agent, or Firm*—Cushman, Darby & Cushman

[57] ABSTRACT

Aroma and/or flavor materials for use in baking such as in making sourdough bread are produced by culturing lactic acid bacteria in an aqueous dispersion of an expanded, pregelatinized, starch-containing cereal adsorbent. The cereal adsorbent is obtained by extrusion of a cereal product under a pressure of less than 50 bar at a temperature of at least 150° C. A 10 wt% dispersion of the cereal adsorbent has a viscosity at 25° C. of about 30 to about 60 mPas. After culturing, a concentrate substantially free from insoluble matter is separated. The concentrate is separated by centrifugation into a cell concentrate and a clarified broth containing the aroma and/or flavor materials. The lactic acid bacteria are adsorbed in situ onto the cereal adsorbent during culturing. Insoluble residue separated after culturing contains supported lactic acid bacteria that can be used in making sourdough bread. If necessary, the supported bacteria can be dried for storage before use.

4 Claims, No Drawings

PRODUCTION OF AROMA AND/OR FLAVOR MATERIALS WITH LACTIC ACID BACTERIA SUPPORTED ON AN EXPANDED, CEREAL ADSORBENT

This application is a division of application Ser. No. 07/601,129, filed Oct. 23, 1990, now abandoned.

This application is related to application Ser. No. 07/930,452, filed Aug. 19, 1992, now U.S. Pat. No. 5,211,971, which is a continuation of application Ser. No. 07/601,129.

This invention relates to fermentation processes having an industrial and culinary application. In particular, the invention relates to the use of growth nutrient for culturing lactic acid micro-organisms for such processes. The invention also relates to new supported lactic acid bacteria cultures, to the preparation of compositions containing aroma and/or flavours, to the use of the cultures in the production of these aroma and/or flavour compositions and to baking operations using these compositions.

Fermentation processes are widely applied in industrial and culinary processes, simple examples being the use of the yeast Saccharomyces in bread-making and lactic acid bacteria in sourdough bread-making.

Micro-organisms are also used in the industrial production of alcohol and acetone, silage and many other products, particularly in the food industry.

Micro-organisms must first be cultured on a suitable nutrient growth medium, which must be active to provide the necessary growth factors in a readily digestible form. In industrial processes, such as the production of alcohol from yeast fermentation, the culturing is carried out in situ. Lactic acid micro-organisms are, on the other hand, concentrated from a nutrient broth culture and may be adsorbed on an inert support for future use in fermentation processes.

The growth of the micro-organism must be controlled to provide a high final cell density in the product ($10^8$-$5.10^9$/ml). Natural nutrient medium may be difficult to provide, particularly in the case of lactic acid bacteria which are known for their extreme requirements for growth factors, such as vitamins, amino acids and spore elements for which yeast extract and usually also beef extract are the chief cost items comprising conventional nutrient broths for culturing these micro-organisms.

After culturing, the micro-organism is concentrated and may be adsorbed on a suitable granular or powdered inert support. Whereas the nutrient growth medium must provide the ingredients necessary for growth in a readily assimilable form, the support material should be substantially inert to the micro-organism, at least under the contact and storage conditions, and should prevent deterioration of the viable count and be generally stable at ambient conditions for good storage.

The present invention provides excellent nutrient growth material for lactic acid-producing micro-organisms. It has been surprisingly discovered that a suitable nutrient for culturing lactic acid bacteria comprises a pre-gelatinised, expanded starch-containing cereal medium which may be obtained by extrusion under suitable conditions of temperature, pressure and moisture content. The expanded products are friable and have a high surface area capable of adsorbing substantial amounts of liquid while remaining a flowable powder or granular material.

PRIOR ART

German patent specification 3206751 describes a method for producing expanded starch-containing cereal products by extrusion under the influence of a specified temperature range and in the presence of a gassing agent. In our co-pending European patent application 0303460 a high temperature range, i.e. above 150° C., is proposed for the extrusion of starch, under which an expanded product may be obtained having a high capacity for adsorbing liquid, such as vegetable oils, while remaining free-flowing, even without using gassing agents. In our co-pending European patent application 298605 it is proposed to employ pre-dried flour as a support for lactic acid bacteria. According to European patent specification 63438 (Scottish Milk Marketing Board) milk powder has been proposed as a support.

A variety of wheat and other cereal products has been proposed as nutrient media for culturing micro-organisms, for example, steamed and enzymatically treated rye and wheat flour for the culturing of lactic acid bacteria, according to J. Food Eng. 1983, pages 177-187. Extruded wheat has also been reported as an effective nutrient for the manufacture of ethanol by yeast fermentation in situ.

DESCRIPTION OF THE INVENTION

The present invention provides a process of producing lactic acid bacteria cultures in which a lactic acid-producing micro-organism is cultured by inoculation of an aqueous nutrient growth medium and optionally a separation step in which the bacterial product is concentrated, preferably with a viable count of at least $10^8$/ml and preferably adsorbing the concentrate on a suitable support, wherein the nutrient growth medium comprises an aqueous dispersion of an expanded, pre-gelatinised starch-containing cereal adsorbent, preferably extruded under conditions, particularly of temperature, pressure and water content, to an extrusion product which in a 10 wt.% aqueous dispersion exhibits a viscosity less than 80 mPa s at 25° C., after effective dispersion and standing for 90 minutes to promote dissolution of soluble matter. Viscosity determinations are obtained by Haake Roto-visco instrument, a rotating cylinder-type viscometer.

The invention also provides new supported lactic acid bacteria cultures wherein the support consists of an expanded, preferably extruded, pre-gelatinised starch-containing cereal adsorbent. The viable count of the bacteria is at least $10^8$/ml.

The application of expanded cereal products for culturing lactic acid bacteria according to the invention is particularly valuable, since the yeast and beef extracts normally necessary in culture broth for this purpose may be dispensed with, only a source of carbon, such as glucose, with trace elements normally being desirable in addition. Preferably, the starch-containing cereal source is extracted rye flour but may also comprise unmilled grain including rye bran, since it has been found that lactic acid bacteria supported on these rye-based compositions are particularly suitable for bread-making by the sourdough method. The flour or other material may be prepared in accordance with the method described in EP 303460 and used additionally to provide a supported micro-organism in accordance with the method described in EP 298605. Other supports may, however, be used, for example powdered milk and vegetable starch extracted from seed crops, cassava or potato starch. Alternatively, the cultures of the present invention may be used directly in breadmaking.

Following inoculation and growth in the nutrient growth medium, an insoluble residue may be separated from the broth comprising insoluble, expanded pregelatinised starch-containing extruded rye flour residues on which the micro-organism is adsorbed in situ. This composition may be dried, if necessary, for storage before use.

An important advantage of the present invention is that mixed cell starter systems, e.g. Böcker ® systems, and hetero-fermentative systems, which cannot normally be grown on beef broth alone, can be readily cultured on nutrient growth media comprising the extruded rye material of the present invention.

Other advantages of the use of the expanded, pre-gelatinised cereal adsorbents reside in that high temperatures are used during the extrusion, so that the growth material can be sterilized separately from the water phase, resulting in a fermentation medium with fewer heat-induced reaction products (Maillard products) present. Further, a mechanically treated support, i.e. a more finely divided support, is used, as a result of which the building up of the desired count is faster, while also the maximum viable count is higher.

Moreover, this system provides the possibility of adding a culture, grown on a medium, that is identical with the system wherein the culture is finally applied.

Preferably, the rye is pre-gelatinised during extrusion. Extrusion conditions are preferably selected to provide less viscous broth, which is more readily concentrated by centrifuge. Both *L. brevis* (var. linder) and Böcker ® strains can be grown to cell densities comparable with those obtained with conventional media containing both yeast and beef extracts. After separation from insoluble matter, the concentrate may be concentrated, preferably centrifuged, to provide cell concentrate and a clarified broth-containing lactic acid and aroma and flavour materials, which may be concentrated, preferably spray-dried, and used in baking operations.

Therefore, part of the invention is also a method for the preparation of a composition containing lactic acid and aroma and/or flavour materials, wherein the culture containing lactic acid-producing micro-organism is produced according to the invention, after which the concentrate thus obtained is separated, producing a cell concentrate and a clarified broth, which broth can be concentrated, preferably spray-dried, at about ambient temperature. In this way, nearly all the flavours present in the culture are obtained in a concentrated form in the broth or in its concentrated product.

The compositions containing aroma and/or flavour materials which can be obtained according to this process and which are very useful baking ingredients are also part of the invention.

Yet another part of our invention is the use of the cereal dispersions of our invention, inoculated with lactic acid-producing micro-organisms, for the production of compositions containing flavour and/or aroma materials.

Moreover, our invention is concerned with baking operations, wherein the above-mentioned broth or its concentrated product is used as flavouring material.

In the preparation of extruded flour for use in the present invention, the composition to be extruded preferably contains less than 10 wt.% added water, particularly 5% or less added water, if any. The mixture may be aerated during extrusion, for example by incorporating an aerating agent, e.g. ammonium bicarbonate or baking powder, in the mixture being extruded. The amount of any aerating agent present can be from 0.1 to 1% by weight of the extrusion mixture. Where a gassing agent is adopted, preferably ammonium bicarbonate is used.

Extrusion is preferably effected at a temperature of at least 150° C., more preferably 150° to 300° C., most preferably 200°–300° C., with internal temperatures up to 350° C., at which the starch content of the extrusion mix is gelatinised. High extrusion pressures yield products providing high viscosity suspensions, which are less desirable since separation of insoluble matter after inoculation and growth is more difficult and also because, although viscosity is substantially reduced after fermentation, it may nevertheless be too high to permit adequate growth rates and ready recovery of cells. High initial viscosity results in high, albeit considerably reduced, viscosity after fermentation. Preferably, the extrusion pressure is less than 50 bar, especially 20 to 35 bar. The amount of moisture present, the temperature, extrusion orifices and the feed rate all contribute to the pressure required for extrusion and high pressure results in high viscosity when the extrudate is dispersed. Preferably, the viscosity of a 10% aqueous suspension of the extrudate is from 30 to 60 mPa s, relating to an extrusion pressure of approximately 25 to 35 bar. Viscosity of the nutrient medium decreases substantially during fermentation, from between 30 and 40 mPa s to 5–8 mPa s, i.e. of the same order of magnitude as traditional fermentation media for homo-fermentative lactobacilli. Fermentation maximal growth rate under these conditons, calculated as the doubling time, is 2–3 hours in the presence of glucose and 4–5 hours without glucose. Suitable extrusion equipement consists of a generally cylindrical casing enclosing a pair of parallel, co-rotatable feed-screws, along the length of which the starch is delivered from a hopper at the back of the device, forward to an extrusion plate at the front, the plate being, for example, 5 cm in diameter and furnished with extrusion orifices 1.5–5 mm in diameter.

The extrusion conditions may require adjustment according to the material to be extruded, in order to keep the extrusion pressure within the prescribed limits preferred. Thus, for a more open extrusion orifice the extrusion pressure is lower at a given mass flow.

EXAMPLES

Milled German rye flour type T1150 containing 13 wt.% moisture was extruded with a Clextral BC45 extruder fitted with twin flights screw elements and one reverse element. Throughputs were employed in the range of from 18 to 45 kg/h and the product temperature of the die exit was from 200° C. to 231° C.; under these conditions the pressure in the extruder ranged from 23 to 69 bar. The moisture content of the extruded rye was approximately 5%. Further particulars of extrusion conditions in the different Examples appear in Table 1.

The extruded rye was suspended in water to a concentration of 10%. Adequate mixing of the slurry was obtained by using an Ultra Torrax high speed mixer (Ika Labortechnik). After standing for 90 minutes, the viscosity of the slurry was measured at 25° C.

TABLE 1

|  | CONTROL | | EXAMPLE | | |
| --- | --- | --- | --- | --- | --- |
|  | 1 | 2 | 1 | 2 | 3 |
| Product temp. (°C.) | 231 | 224 | 217 | 216 | 200 |
| H$_2$O dosage (kg/h) | 1.2 | — | — | — | — |
| Flour flow (kg/h) | 18.0 | 45.0 | 18.5 | 21.0 | 19.6 |
| Screw (r.p.m.) | 201 | 202 | 201 | 293 | 293 |
| Pressure (bar) | 67 | 69 | 33 | 25 | 23 |
| Die (no. × dia.mm) | 8 × 1 | 8 × 1 | 8 × 1 | 4 × 4 | 4 × 4 |
| Viscosity (mPas) | 141 | 181 | 42 | 37 | 17 |
|  | Viscosity too high to operate a complete fermentation process. | | Acceptable viscosity for fermentation process. | | |

To the suspension of Example 2, 50 g/1 glucose, 0.1 M KH$_2$PO$_4$ buffer (pH 6.5) and 0.1 M ammonium dicitrate was added also to obtain a nutritionally balanced fermentation medium after removing large insoluble particles by centrifugation. The medium autoclaved at 100° C. for 10 minutes for pasteurisation.

Fermentation was conducted in a fermentor incubated anaerobically at 30° C., using the extrusion product of Example 2 as medium. After inoculation, the initial cell count was approximately 10$^7$ cells/gram.

The following strains were used in separate experiments as an inoculum for growth:

A. *Lactobacillus brevis* (var. lindneri) in a liquid culture.

B. Böcker ® starter culture (50 g of starter culture powder diluted in 150 ml water).

After growth, the cells were concentrated by centrifuge.

Viable counts determination.

Dilutions of the samples were made in peptone-NaCl solution. Aliquots of 1 ml of the proper dilutions were mixed with agar at a temperature of approximately 45° C. (pour plate method). MRS plates (Merck-Diagnostical) was used for viable count determinations of lactobacilli. This medium was prepared, according to the instructions of the manufacturer, directly before use and contained 62 g/1 MRS, 0.3% lecithin and 0.4% D-L-lactic acid 88% (Analar). Plates were incubated anaerobically at 30° C. for 2 days. Viable counts were determined on 10% rye in separate experiments with and without added supplements for homo- and hetero-fermentative cultures. No significant pH change was observed and no lactic acid was detected from Böcker ® cultures. Results are given in Table 2.

TABLE 2

| Supplement wt. % | | | Viable Count × 10$^8$ | | Lactic Acid wt. % |
| --- | --- | --- | --- | --- | --- |
| Vitamins | Yeast Extract | Glucose | L.Brevis | Bocker ® | L.Brevis |
| Nil | Nil | Nil | 1.2 | 5.2 | 0.74 |
| Nil | 0.1 | Nil | 1.1 | — | 0.79 |
| Nil | 1.0 | 0.2 | 5.0 | — | 1.47 |
| Nil | Nil | 0.5 | 4.0 | 5.3 | 0.97 |
| Nil | 0.1 | 0.5 | 4.1 | — | 1.07 |
| Yes | Nil | Nil | — | 7.2 | — |
| Yes | Nil | 0.5 | — | 3.2 | — |

From Table 2 it is clear that *L. Brevis* is successfully cultured on the extruded rye flour suspension, without the presence of yeast extract, but that an additional carbon source, such as glucose, is desirable, probably owing to the inadequate amylolytic activity of the micro-organism. Further, for the mixed homo- and heterofermentative culture, e.g. Böcker ®, neither yeast nor glucose is required, but that growth benefits from the addition of vitamins. *L. Brevis* could not be processed successfully by using the media of the control example 1 or 2. Although the micro-organism grew on the support, it was impossible to separate the culture because of the high viscosity.

We claim:

1. A method for the preparation of clarified broth containing lactic acid and aroma and/or flavor materials comprising:
    culturing a lactic acid producing bacteria in an aqueous dispersion of an expanded, pre-gelatinized, starch-containing cereal adsorbent obtained by extrusion of a cereal product under a pressure of less than 50 bar at a temperature of at least 150° C., said dispersion having a viscosity at 25° C. of from about 30 to about 60 mPas, when measured as a 10 wt% dispersion,
    separating a concentrate substantially free from insoluble matter, from the aqueous dispersion after said culturing,
    separating said concentrate by centrifugation into a cell concentrate and a clarified broth containing said lactic acid and aroma and/or flavor materials.

2. The method of claim 1 wherein said broth is then further concentrated.

3. The method of claim 2 wherein said broth is further concentrated by spray drying at ambient temperature.

4. The process of claim 1 wherein the broth containing lactic acid and aroma and/or flavor materials is used as an ingredient in making sourdough bread.

* * * * *